US008163702B2

(12) United States Patent
Tuthill et al.

(10) Patent No.: US 8,163,702 B2
(45) Date of Patent: Apr. 24, 2012

(54) TREATMENT OF MELANOMA

(75) Inventors: Cynthia W. Tuthill, Menlo Park, CA (US); Alfred R. Rudolph, Los Altos Hills, CA (US)

(73) Assignee: SciClone Pharmaceuticals, Inc., Foster City, CA (US)

( * ) Notice: Subject to any disclaimer, the term of this patent is extended or adjusted under 35 U.S.C. 154(b) by 460 days.

(21) Appl. No.: 12/297,699

(22) PCT Filed: Apr. 13, 2007

(86) PCT No.: PCT/US2007/009049
§ 371 (c)(1),
(2), (4) Date: Oct. 20, 2008

(87) PCT Pub. No.: WO2007/123847
PCT Pub. Date: Nov. 1, 2007

(65) Prior Publication Data
US 2009/0088392 A1 Apr. 2, 2009

Related U.S. Application Data

(60) Provisional application No. 60/793,243, filed on Apr. 20, 2006.

(51) Int. Cl.
*A61K 38/05* (2006.01)
*A61K 38/00* (2006.01)
(52) U.S. Cl. ............ 514/21.91; 514/1.1; 514/19.8
(58) Field of Classification Search .......... None
See application file for complete search history.

(56) References Cited

U.S. PATENT DOCUMENTS

| 4,758,551 | A |   | 7/1988 | Meister et al. |
|-----------|---|---|--------|----------------|
| 5,595,756 | A | * | 1/1997 | Bally et al. ............ 424/450 |
| 5,744,452 | A |   | 4/1998 | Kolobov et al. |
| 5,877,147 | A |   | 3/1999 | Pinegin |
| 5,916,878 | A |   | 6/1999 | Kolobov et al. |

FOREIGN PATENT DOCUMENTS

| RU | 2091389 C1 | 9/1997 |
| WO | 9719691 A1 | 6/1997 |

OTHER PUBLICATIONS

Definition of derivative from http://cancerweb.ncl.ac.uk/omd/about.html, pp. 1-5. Accessed Jul. 7, 2005.*
Sporn MB, Suh N, "Chemoprevention of cancer," Carcinogenesis, 2000, 21(3): 525-530.*
Auerbach R, Akhtar N, Lewis RL, Shinners, BL, "Angiogenesis assays: Problems and pitfalls," Cancer and Metastais Reviews, 2000, 19: 167-172.*
Gura T, "Systems for Identifying New Drugs Are Often Faulty," Science, 1997, 278: 1041-1042.*
Jain RK, "Barriers to Drug Delivery in Solid Tumors," Scientific American, 1994, 58-65.*
Introduction to cancer from Merck manual, p. 1, Accessed Mar. 5, 2008.*
Clinical Aspects of Cancer from Merck manual, pp. 1-4. Accesssed Mar. 5, 2008.*
Melanoma from Merck manual, pp. 1-4. Accessed Jan. 12, 2011.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Cancer Drug Design and Discovery Neidle, Stephen, ed. (Elsevier/Academic Press, 2008) pp. 427-431.*
PCT/US07/09049 International Search Report mailed Apr. 15, 2008.
PCT/US07/09049 IRPR and Written Opinion mailed Oct. 30, 2008.
PK Appln 443/2007 Office Action, Jul. 29, 2009.
EA Appln 200802136 Office Action dated Apr. 28, 2010.
PK Appln 443/2007 Office Action, Aug. 18, 2010.
Kris, M.G. et al., Phase I Trial and Clinical Pharmacological Evaluation of 10-Ethyl-10-deazaaminopterin in Adult Patients with Advanced Cancer, Cancer Research, Oct. 1, 1988, pp. 5573-5579, vol. 48.
Kris, M.G. et al., Assessment of Pretreatment Symptoms and Improvement after EDAM+mitomycin+vinblastine(EMV) in Patients(PTS) with Inoperable Non-Small Cell Lung Cancer(NSCLC), Proceedings of ASCO, Mar. 1990, p. 229, vol. 9.
Ohe, Yuichiro et al., In Vitro Evaluation of the New Anticancer Agents KT6149, MX-2, SM5887, Menogaril and Liblomycin Using Cisplatin- or Adriamycin-resistant Human Cancer Cell Lines, Aug. 1, 1989, pp. 4098-4102, vol. 49.
Savarese, Diane M.F. et al., Prevention of Chemotherapy and radiation toxicity with glutamine, Cancer Treatment Reviews, 2003, pp. 501-513, vol. 29.
Sirotnak, F. M. et al, 10-Ethyl-10-Deaza-aminopterin: Structural Design and Biochemical, Pharmacologic, and Antitumor Properties, NCI Monographs, 1987, pp. 127-131, vol. 5.
Smith, D. Lynne et al., Natural Killer Cell Cytolytic Activity is Necessary for in Vivo Antitumor Activity of the Dipeptide L-Glutamyl-L-Tryoptophan, Int. J. Cancer, 2003, pp. 528-533, vol. 106.

* cited by examiner

*Primary Examiner* — Julie Ha
(74) *Attorney, Agent, or Firm* — Cooley LLP

(57) ABSTRACT

An immunomodulatory compound is administered to treat, prevent, inhibit, or reduce melanoma in a subject.

21 Claims, 2 Drawing Sheets

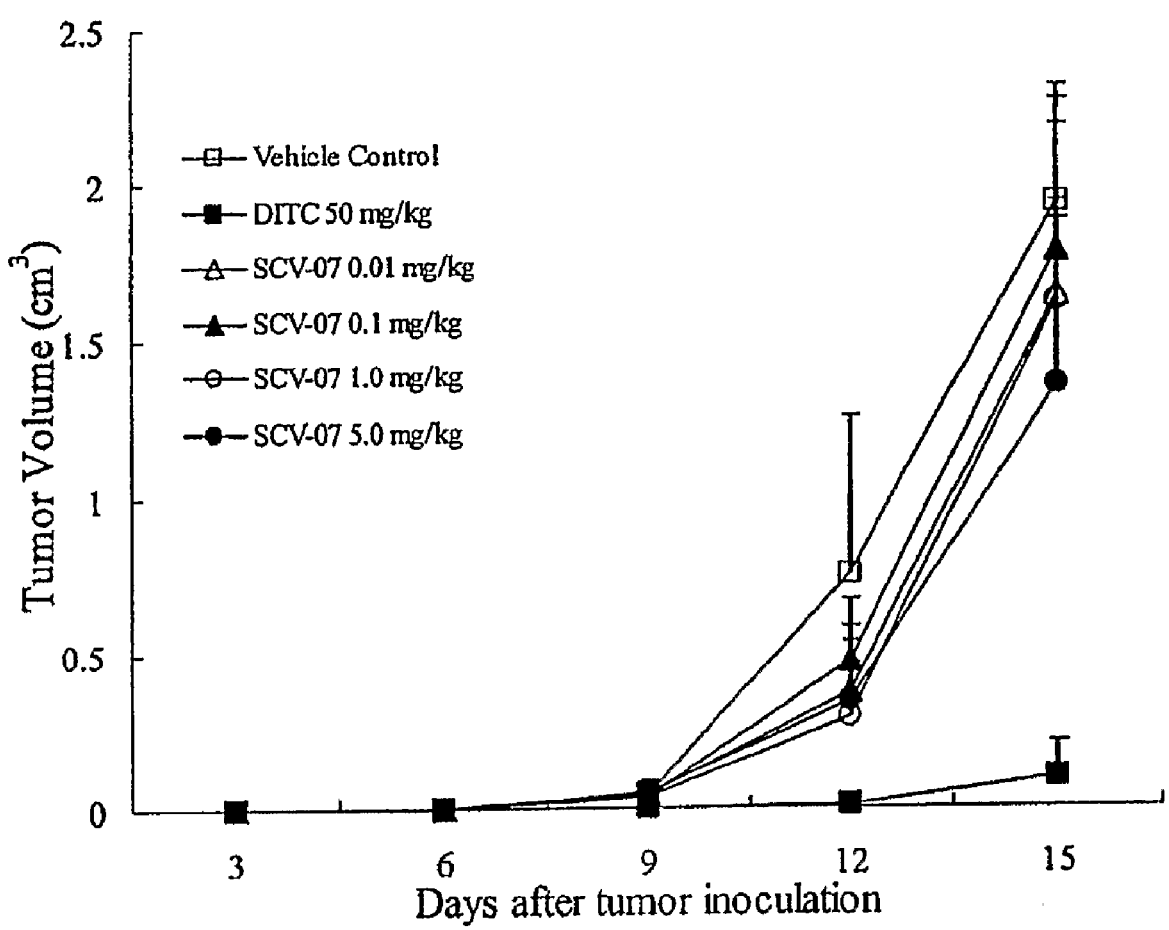
Figure 1: Tumor growth curve

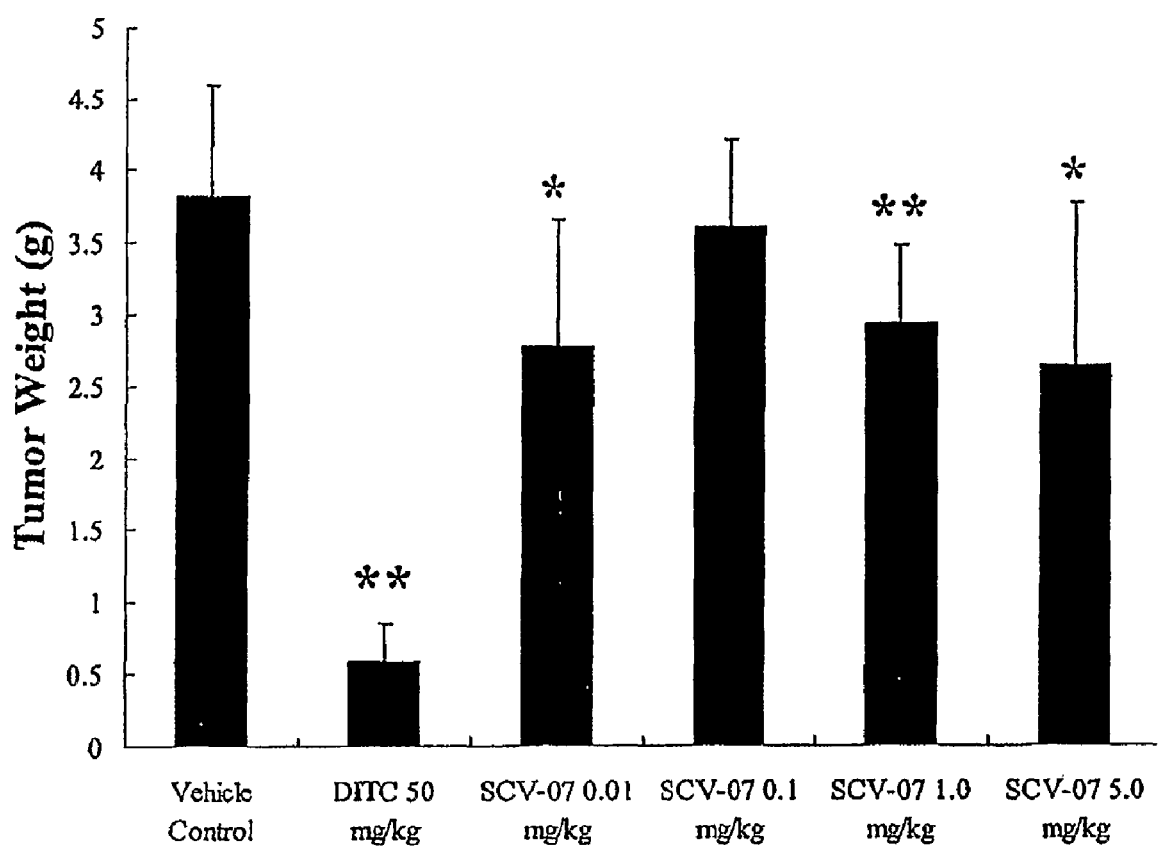
Figure 2: Tumor Weight
* $p<0.05$; ** $p<0.01$

TREATMENT OF MELANOMA

CROSS REFERENCE TO RELATED APPLICATION(S)

This application is a 35 U.S.C. §371 National Phase Entry Application from PCT/US2007/009049, filed Apr. 13, 2007, and designating the United States. This application also claims the benefit of U.S. Patent Application No. 60/793,243, filed Apr. 20, 2006, the disclosure of which is incorporated herein in its entirety by reference.

BACKGROUND OF THE INVENTION

1. Field of the Invention

The present invention relates to the field of treatment of melanoma.

2. Description of Background Art

Melanoma is a malignant tumor of melanocytes. Primarily it is a skin tumor, but it is also seen, though less frequently, in the melanocytes of the eye (uveal melanoma). Even though it represents one of the rarer forms of skin cancer, melanoma underlies the majority of skin cancer-related deaths. Despite many years of intensive laboratory and clinical research, the sole current effective cure is surgical resection of the primary tumor before it achieves a thickness of greater than 1 mm.

Melanoma of the skin accounts for 160,000 new cases worldwide each year, and is more frequent in white men. It is particularly common in white populations living in sunny climates. According to the WHO Report about 48,000 deaths worldwide due to malignant melanoma are registered annually.

The diagnosis of melanoma requires experience, as early stages may look identical to harmless moles or not have any color at all. Moles that are irregular in color or shape are suspicious of a malignant melanoma or a premalignant lesion.

The current treatments include surgical removal of the tumor with adjuvant treatment; chemo- and/or immuno-therapy, and/or radiation therapy.

Generally, an individual's risk for developing melanoma depends on two groups of factors: intrinsic and environmental. "Intrinsic" factors are generally an individual's family history and inherited genotype, while the most relevant environmental factor is sun exposure.

Epidemiologic studies suggest that exposure to ultraviolet radiation (UVA and UVB) is one of the major contributors to the development of melanoma. UV radiation causes damage to the DNA of cells, which when unrepaired can create mutations in the cell's genes. When the cell divides, these mutations are propagated to new generations of cells. If the mutations occur in oncogenes or tumor suppressor genes, the rate of mitosis in the mutation-bearing cells can become uncontrolled, leading to the formation of a tumor. Occasional extreme sun exposure (resulting in "sunburn") is causally related to melanoma. Other factors are mutations in or total loss of tumor suppressor genes. Use of sunbeds (with deeply penetrating UVA rays) has been linked to the development of skin cancers, including melanoma.

Possible significant elements in determining risk include the intensity and duration of sun exposure, the age at which sun exposure occurs, and the degree of skin pigmentation. Exposure during childhood is a more important risk factor than exposure in adulthood. This is seen in migration studies in Australia where people tend to retain the risk profile of their country of birth if they migrate to Australia as an adult. Individuals with blistering or peeling sunburns (especially in the first twenty years of life) have a significantly greater risk for melanoma.

Fair and red-headed people, persons with multiple atypical nevi or dysplastic nevi and persons born with giant congenital melanocytic nevi are at increased risk.

A family history of melanoma greatly increases a person's risk because mutations in CDKN2A, CDK4 and several other genes have been found in melanoma-prone families. Patients with a history of one melanoma are at increased risk of developing a second primary tumour.

The incidence of melanoma has increased in the recent years, but it is not clear to what extent changes in behavior, in the environment, or in early detection are involved.

Familial melanoma is genetically heterogeneous, and loci for familial melanoma have been identified on the chromosome arms 1p, 9p and 12q. Multiple genetic events have been related to the pathogenesis of melanoma. The multiple tumor suppressor 1 (CDKN2A/MTS1) gene encodes p16INK4a—a low-molecular weight protein inhibitor of cyclin-dependent protein kinases (CDKs)—which has been localised to the p21 region of human chromosome 9.

There remains a need in the art for methods of treatment for treating, preventing, inhibiting or reducing melanoma.

SUMMARY OF THE INVENTION

In accordance with the present invention, a method of treatment for treating, preventing, inhibiting or reducing melanoma or a metastasis thereof, or for treating, preventing, inhibiting or reducing growth of melanoma cells or metastases thereof, in a subject, comprises administering to the subject a melanoma treatment-effective amount of an immunomodulator compound of formula A

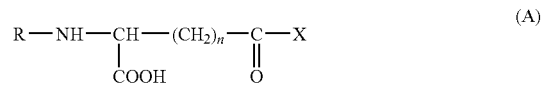

(A)

wherein, n is 1 or 2, R is hydrogen, acyl, alkyl or a peptide fragment, and X is an aromatic or heterocyclic amino acid or a derivative thereof, so as to treat, prevent, inhibit or reduce said melanoma or metastasis thereof in the subject, or treat, prevent, inhibit or reduce growth of said melanoma cells or metastases thereof in the subject.

BRIEF DESCRIPTION OF THE DRAWINGS

FIG. 1 graphically depicts tumor growth in one study of one embodiment at different dosages.

FIG. 2 graphically depicts tumor weight in the study of one embodiment at different dosages.

DESCRIPTION OF THE PREFERRED EMBODIMENTS

In accordance with one embodiment, the present invention relates to a method of treatment for treating, preventing, inhibiting, or reducing melanoma by administering an immunomodulator compound to a mammalian subject, preferably a human patient.

In one embodiment, the disease is melanoma or a metastasis thereof. The invention can be utilized to treat, prevent, inhibit or reduce growth of melanoma cells or metastases thereof in a subject. Preferably, the primary melanoma is removed by surgery before, during or after treatment with a compound of the invention.

Immunomodulator compounds in accordance with the present invention comprise immunomodulators of Formula A:

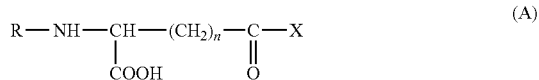

(A)

In Formula A, n is 1 or 2, R is hydrogen, acyl, alkyl or a peptide fragment, and X is an aromatic or heterocyclic amino acid or a derivative thereof. Preferably, X is L-tryptophan or D-tryptophan, most preferably L-tryptophan.

Appropriate derivatives of the aromatic or heterocyclic amino acids for "X" are: amides, mono- or di-$(C_1-C_6)$alklyl substituted amides, arylamides, and $(C_1-C_6)$alkyl or aryl esters. Appropriate acyl or alkyl moieties for "R" are: branched or unbranched alkyl groups of 1 to about 6 carbons, acyl groups from 2 to about 10 carbon atoms, and blocking groups such as carbobenzyloxy and t-butyloxycarbonyl. Preferably the carbon of the CH group shown in Formula A has a stereoconfiguration, when n is 2, that is different from the stereoconfiguration of X.

Preferred embodiments utilize compounds such as γ-D-glutamyl-L-tryptophan, γ-L-glutamyl-L-tryptophan, γ-L-glutamyl-$N_{in}$-formyl-L-tryptophan, N-methyl-γ-L-glutamyl-L-tryptophan, N-acetyl-γ-L-glutamyl-L-tryptophan, γ-L-glutamyl-D-tryptophan, β-L-aspartyl-L-tryptophan, and β-D-aspartyl-L-tryptophan. Particularly preferred embodiments utilize γ-D-glutamyl-L-tryptophan, sometimes referred to as SCV-07. These compounds, methods for preparing these compounds, pharmaceutically acceptable salts of these compounds and pharmaceutical formulations thereof are disclosed in U.S. Pat. No. 5,916,878, incorporated herein by reference.

SCV-07, γ-D-glutamyl-L-tryptophan, is a member of a class of immunomodulatory drugs that possess γ-glutamyl or β-aspartyl moieties, which was discovered by Russian scientists and is being examined for efficacy in several indications in the U.S. by SciClone Pharmaceuticals, Inc. SCV-07 possesses a number of immunomodulatory activities in vivo and in vitro. SCV-07 increases Con-A-induced thymocyte and lymphocyte proliferation, increases Con-A-induced interleukin-2 (IL-2) production and IL-2 receptor expression by spleen lymphocytes, and stimulates expression of Thy-1.2 on bone marrow cells. In vivo, SCV-07 has a strong immunostimulatory effect on 5-FU-immune-suppressed animals and in a model of immunization with sheep red blood cells.

The Formula A compounds may be administered at any effective dosage, e.g., at dosages in the range of about 0.001-1000 mg, preferably about 0.1-100 mg and most preferably about 10 mg. Dosages may be administered one or more times per week, e.g., on a daily basis, with dosages administered one or more times per day. Administration can be by any suitable method, including orally, nasally, transdermally, sublingually, by injection, periodic infusion, continuous infusion, and the like. The dosages may be administered by intramuscular injection, although other forms of injection and infusion may be utilized, and other forms of administration such as oral or nasal inhalation or oral ingestion may be employed. Aerosols, solutions, suspensions, dispersions, tablets, capsules, syrups, etc., may be utilized.

Dosages may also be measured in milligrams per kilogram, with dosages in the range of about 0.00001-100 mg/kg, more preferably within the range of about 0.01-10 mg/kg.

Included are biologically active analogs having substituted, deleted, elongated, replaced, or otherwise modified portions which possess bioactivity substantially similar to that of SCV-07, e.g., an SCV-07 derived peptide having sufficient homology with SVC-07 such that it functions in substantially the same way with substantially the same activity as SCV-07.

According to one embodiment, a Formula A compound may be administered to a subject so as to substantially continuously maintain an effective amount of the Formula A compound in the subject's circulatory system during a treatment or prevention period. Although much longer treatment periods are contemplated in accordance with the present invention, embodiments of the invention include substantially continuously maintaining an effective amount of the Formula A compound in the patient's circulatory system during treatment periods of at least about 6, 10, 12 hours, or longer. In other embodiments, treatment periods are for at least about a day, and even for a plurality of days, e.g., a week or longer. However, it is contemplated that treatments, as defined above, in which effective amounts of the Formula A compound are substantially continuously maintained in the subject's-circulatory system, may be separated by non-treatment periods of similar or different durations.

In accordance with one embodiment, the Formula A compound is continuously infused into a subject, e.g., by intravenous infusion, during the treatment period, so as to substantially continuously maintain an effective amount of the Formula A compound in the subject's circulatory system. The infusion may be carried out by any suitable means, such as by minipump. Alternatively, an injection regimen of the Formula A compound can be maintained so as to substantially continuously maintain an effective amount of the Formula A compound in the subject's circulatory system. Suitable injection regimens may include an injection every 1, 2, 4, 6, etc. hours, so as to substantially continuously maintain the effective amount of the Immunomodulator compound peptide in the subject's circulatory system during the treatment period.

Although it is contemplated that during continuous infusion of the Formula A compound, administration will be for a substantially longer duration, according to one embodiment the continuous infusion of the Formula A compound is for a treatment period of at least about 1 hour. More preferably, continuous infusion is carried out for longer periods, such as for periods of at least about 6, 8, 10, 12 hours, or longer. In other embodiments, continuous infusion is for at least about one day, and even for a plurality of days such as for one week or more.

In some embodiments, the Formula A compound is present in a pharmaceutically acceptable liquid carrier, such as water for injection, physiological saline, or similar, at concentrations within a range of about 0.001-1000 µg/ml, more preferably about 0.1-100 µg/ml.

Effective amounts of Formula A compound can be determined by routine dose-titration experiments.

The Formula A compound also can be administered with other agents. For example, with treatments of cancer such agents include chemotherapy agents and/or radiation.

EXAMPLE 1

Introduction

SCV-07 (γ-D-glutamyl-I-tryptophan) is a synthetic dipeptide that has demonstrated immunomodulatory activity by increasing T-cell differentiation and function, biological processes that are necessary to control in vivo tumor growth.

One of the striking advances in the last decade is that the polarization of an immune response from the TH(CD4+ T cells) type one (TH1) towards the type two (TH2) phenotype contributes to a decreased cellular immunity against cancer, and that cytokines play a pivotal role in the development of tumors by regulating the expansion of TH1 and TH2 cells.

Previous studies with SCV-07 show that this immunomodulatory compound stimulates a shift of T helper cells towards a TH1-like immune response, and that IFN-γ production by both thymic and spleen cells, as well as its circulating level in serum, is increased by SCV-07 treatment.

Melanoma is the prototype of an immunogenic tumor, to which various types of immunotherapy have been applied. In the present study we investigated the in vitro and in vivo biological activity of SCV-07 using a murine B16 melanoma model.

Methods

Tumors were induced by injecting 1×10⁶ B16 melanoma cells subcutaneously in the hind leg of C57/Bl6 syngeneic mice. Mice were randomized into 5 groups of 10 animals and treated with SCV-07 at doses of 0.001, 0.01, or 0.10 mg/kg administered daily i.p. for 3 consecutive days for 2 weeks, starting 3 days after tumor implantation. Control groups were treated with saline or dacarbazine (DTIC) at a dose of 50 mg/kg i.p. for 3 days. Tumor growth was assessed every 3 days by a caliper and tumor weight was measured upon death.

In vitro cell sensitivity studies were performed on a B16 cell line. Subconfluent melanoma cells were harvested, suspended in complete medium and seeded into 24-well plates (10⁵ cells in a final volume of 2 ml/well). The cells were treated in triplicate wells for 24, 48 or 72 hr of culture with graded concentrations of SCV-07 ranging from 0.1 to 100 μg/ml. Cell proliferation and viability were determined by the trypan blue dye exclusion method by manually counting the cells with a hemocytometer.

Apoptosis was assessed by DNA flow cytometric analysis. At each concentration of SCV-07, adherent cells were detached from the plates by trypsinization, pooled with the floating cells and fixed with 50% acetone:methanol 1:4 in PBS. The cells were suspended (1×10⁶/ml) in PBS containing 50 μg/ml of propidium iodide (PI) and 100 KU/ml of RNase and incubated in the dark at room temperature for 30 min. The DNA content per cell was evaluated by PI fluorescence measured on a linear scale using a FACScan flow cytometer (Becton & Dickinson, San Jose, Calif.). Apoptotic cells show a diminished staining, in the red fluorescence channel, below the G0/G1 population of normal diploid cells, and are represented by a broad hypodiploid peak due to DNA fragmentation following apoptotic events. This is easily distinguishable from the narrow peak of cells with diploid DNA content. The fraction of apoptotic cells was therefore calculated by integrating the pre-G1 peak.

Results

In Vivo

Mice were injected with B16 melanoma cells and divided into 5 groups of 10 mice each. Control mice were given injections of saline or dacarbazine (DTIC). The effects of different doses of SCV-07 were examined with respect to tumor growth rate and survival time.

The results show that SCV-07 inhibited tumor growth in a dose-dependent manner, as illustrated in Table A. After 24 days, the inhibition in tumor growth was 6%, 22.6%, and 42.7% for the 0.001, 0.01 and 0.1 mg/kg treatments respectively, vs. control (DTIC treatment led to a 19.0% inhibition).

TABLE A

| GROUPS | treatment dose (mg/kg) | DAY 10 | DAY 17 | DAY 24 | DAY 24 |
|---|---|---|---|---|---|
| | | MEAN TUMOR VOLUME (mm³ ± SD) | | | |
| Buffered saline | — | 560 ± 120 | 661 ± 180 | 930 ± 240 | % of control |
| DTIC | 50 | 480 ± 13 | 545 ± 170 | 760 ± 220 | 19 |
| SCV-07 | 0.001 | 540 ± 180 | 625 ± 270 | 880 ± 240 | 5.5 |
| SCV-07 | 0.01 | 490 ± 120 | 581 ± 210 | 720 ± 150 | 22.6 |
| SCV-07 | 0.10 | 420 ± 150 | 495 ± 190 | 533 ± 170 | 42.7 |

The mean tumor weight was 35% lower in the animals treated with the highest dose of SCV-07, compared to 20% for the lower doses and 15% for DTIC.

The survival time of mice in the different treatment groups was monitored up to 30 days after tumor injection. After 26 days, 21% of the animals treated with SCV-07 at the highest dose were surviving in good condition, although with tumors. There were no surviving animals in the groups treated with lower doses or with DTIC.

In Vitro

The antiproliferative activity of SCV-07 was evaluated on B16 melanoma growth by direct cell counts after 24 and 48 hrs of culture. The results of a representative experiment, show that SCV-07 induced a dose-dependent inhibitory effect on cell growth in B16. At low concentration the effect of SCV was substantially cytostatic while at higher concentration (100 μg/ml) SCV-07 showed toxic effects with a dramatic decrease in the number of viable cells. However, flow cytometric analysis by propidium iodide could not evidence any significant effect of SCV-07 on the percentage of apoptotic cell death.

Conclusion

The results showed growth inhibition of melanoma cells, both in vitro and in vivo, and show that SCV-07 treatment may be a potential therapeutic strategy as consequence of modulation of host antitumor response and direct killing of tumor cells.

EXAMPLE 2

Antitumor Effect of SCV-07 in Murine B16 Melanoma Model

Abbreviations

DTIC Dacarbazine
F Female
g Gram
IR Inhibition Rate
kg Kilogram
L Length
M Male
mL Milliliter
SD Standard Deviation
W Width

SUMMARY

The antitumor effect of SCV-07 in murine B16 melanoma model was evaluated in this study. A total of 60 C57/BL6 mice, 30 males and 30 females, were implanted subcutaneously with murine B16 melanoma cells followed by treatment for 14 consecutive days. SCV-07 was administered by subcutaneous injection to 5 groups of C57/BL6 mice respectively at doses of 0 (Group 1: vehicle control group), 0.01 (Group 3), 0.1 (Group 4), 1.0 (Group 5) and 5.0 mg/kg/day (Group 6), for 14 consecutive days (Day 1 to Day 14). Dacabazine (DTIC), 50 mg/kg/day, was subcutaneously administered to Group 2 (positive control group) from Day 1 to Day 14. Tumor weights were taken on Day 17 after euthanasia.

No deaths were found in any of the dose groups during the study. The statistical results of body weights showed that there is no significant difference between SCV-07 treated groups and vehicle control group, indicating that SCV-07 has no effect on body weight gain. However, the results showed a significant inhibition of body weight gain (P<0.01) in DTIC treatment group, which is probably the result of DTIC's toxicity.

On Day 3 and Day 6, tumor sizes of all groups were not measurable. The mean tumor sizes of SCV-07 treatment groups on Day 9 did not show statistical differences when compared with the vehicle control group. On Day 12, the mean tumor sizes of Group 3, Group 5 and Group 6 were significantly smaller than Group 1. Although the mean tumor size of Group 4 on Day 12 was smaller than Group 1, the results did not show statistical significance. On Day 15, the mean tumor sizes of Group 3, Group 4, Group 5 and Group 6 were smaller than Group 1, but only the results of Group 5 and Group 6 showed statistical significance. The tumor growth inhibition rate of SCV-07 of Group 6 (highest dose level) on Day 15 was 30.2%, indicating a significant (p=0.01) inhibition of tumor growth when compared to the vehicle control group. Group 5 (dose level of 1.0 mg/kg SCV-07) also showed significant tumor growth inhibition (16.5%) at the end of treatment on Day 15. The tumor growth curves also showed that the tumors grew slower in the SCV-07-treated animals when compared to the vehicle control group. Animals in positive control group have significant decrease of mean tumor sizes. Its inhibition rates of tumor growth were 96.9%, 98.8% and 95.1% on Day 9, Day 12 and Day 15, respectively. This proves that the tumor model used in this study is valid.

On Day 17, the mean tumor weights of all SCV-07 treatment groups were lower than the vehicle control group. However, only the results of Group 3, Group 5 and Group 6 showed statistical significance. The tumor growth inhibition rate of Group 6 was 30.8% (p=0.015) when compared to Group 1. Group 3 and Group 5 also showed significant tumor growth inhibition of 27.5% and 23.5%, respectively. Animals in positive control group have significant decrease of mean tumor weights. Its inhibition rate of tumor weight was 85.0% on Day 17.

In conclusion, the tumor model used in this study is valid. Administration of SCV-07 once daily for 14 consecutive days via the subcutaneous route is effective against murine B16 melanoma tumor growth. Tumor weights in three test-article treated groups were significantly reduced in comparison with those of the vehicle control group. The mean animal body weights of all SCV-07 treatment groups were not significantly different from those of vehicle control group after treatment with SCV-07, supporting the lack of toxicity of the test article. However, although treatment with the positive chemotherapy control, DTIC, decreased the tumor sizes and tumor weights significantly when compared with vehicle control group, it did lead to a significant inhibition of body weight gain. The data of this study indicate that SCV-07 at dose levels of 0.01, 1.0 and 5.0 mg/kg/day for 14 days significantly reduced the B16 melanoma tumor growth without toxic effect on body weight gain.

Introduction

This study was initiated by using transplantable murine B16 melanoma model to assess the effectiveness of SCV-07 as a potential antitumor agent.

Objective

The objective of this study is to evaluate the potential antitumor effect of SCV-07 in a murine B16 melanoma model when administered subcutaneously at dose levels of 0, 0.01, 0.1, 1.0 and 5.0 mg/kg, respectively for 14 consecutive days.

Materials and Methods

Test and Control Articles

Test Article Formulation

Test article SCV-07 was obtained from Sponsor, dissolved in phosphate buffered saline (PBS, NaCl:137 mM, KCl:2.7 mM; K2HPO4:1.4 mM; Na2HPO4:10.1 mM, pH 7.0) to achieve the proper dose levels as indicated in the study design table. The formulation was kept on ice, protected from light, and used within one week. This two-week study required two fresh preparations.

Positive Control Article

Dacarbazine (DTIC) was used as the positive control article. It was purchased from Sigma-Aldrich (code number: D2359) and aliquoted to 10 mg/vial. Before use, one vial was dissolved in PBS to achieve the proper dose level as indicated in the study design table. The formulation was kept on ice, protected from light, and used within one week. This two-week study required two fresh preparations.

Test System and Animal Husbandry

Melanoma Cells

Murine B16 melanoma cells were obtained from Cell Culture Center of Chinese Academy of Medical Sciences (CAMS; Beijing, P.R. China).

Test System

Thirty male and thirty female healthy, naive, C57BL/6 mice were received from the Institute of Laboratory Animal Science, CAMS, Beijing, P.R. China. The animals were six weeks old and weighed between 18 and 22 grams at the start of the study.

Animal Husbandry

Animals were group housed in autoclaved shoe box cages with autoclaved wood chips as the bedding material. The temperature of the animal room was maintained at 22 to 25° C., and the relative humidity was maintained at 40 to 60%. A 12-hour light/12-hour dark cycle was maintained except when interrupted by study-related events. Animals were fed ad libitum with sterile water and Science Australia Unites Efforts Rodent Diet. All animals were acclimated for 3 days before tumor inoculation.

Experimental Procedures

Tumor Cell Preparation

As per aseptic tissue culture procedures, one vial of B16 melanoma cells (supplied by Cell Culture Center of CAMS) was thawed and centrifuged at 1000 rpm, 20-25° C. for 5 minutes. The cell pellets were suspended in 0.1-0.5 mL normal saline (NS) and subcutaneously injected into the right axilla of each mouse (approximately $1 \times 10^6$ cells/mouse). When the tumor diameter was 1 cm approximately (measured by vernier caliper), the animals were euthanized with $CO_2$ asphyxiation and the tumor was excised. Tumor cells were suspended in normal saline as previously described and the cell adaptation cycle was repeated once.

Tumor Cell Inoculation

On Day 0, $1 \times 10^6$ B16 cells in a volume of 0.1 mL normal saline were subcutaneously injected into the right axillary area of the mouse. The day of tumor inoculation was defined as Day 0.

Study Design and Treatment Regimen

On Day 1, the animals were randomized into different groups based on their body weights so that the mean body weights were not statistically significant among groups. Dosing was initiated on Day 1. The test article was administered once daily for 14 consecutive days via subcutaneous (sc) administration in a dose volume of 0.1 mL/20 g body weight. The vehicle was also dosed once daily for 14 consecutive days via sc administration at the same dose volume. The positive control, DTIC, was administered daily via ip administration at the same dose volume.

Each therapy group received different treatment regimens as outlined in the following table.

TABLE 1

Study Design

| Group Number | Treatment | Number of Animals | Dose Level (mg/kg) | Dosing Frequency | Dosing Days | Observation Period | Necropsy Day |
|---|---|---|---|---|---|---|---|
| 1 | Vehicle Control (PBS) | 10 | 0 | Daily, sc | Day 1 to Day 14 | Day 0 to Day 16 | Day 17 |
| 2 | Positive Control (Dacarbazine; DTIC) | 10 | 50 | Daily, sc | | | |
| 3 | SCV-07 | 10 | 0.01 | Daily, sc | | | |
| 4 | SCV-07 | 10 | 0.1 | Daily, sc | | | |
| 5 | SCV-07 | 10 | 1.0 | Daily, sc | | | |
| 6 | SCV-07 | 10 | 5.0 | Daily, sc | | | | sc = Subcutaneous

Antitumor Effect Evaluation

During the observation period, tumor sizes and body weights were measured once every 3 days throughout the study: tumor size by caliper and body weight by laboratory balance. Observations were recorded daily for mortality and moribundity. The animals were euthanized by $CO_2$ asphyxiation on Day 17. The tumors were excised, separated, and weighed.

Tumor volume was calculated using the following formula:

Tumor Volume=Length×Width×Width/2

Tumor volume inhibition rate (IR) was calculated according to the formula:

$IR(TV) = (TV_{vehicle} - TV_{drug\ treated})/TV_{vehicle} \times 100\%$

TV is the tumor volume on the day of measurement.

The antitumor effect of the test article was also evaluated by tumor weight. The tumor weight of each mouse was recorded after euthanasia, and the inhibition rate of tumor weight was calculated according to the formula:

$IR(TW) = (\text{Tumor weight}_{vehicle} - \text{Tumor weight}_{drug\ treated})/\text{Tumor weight}_{vehicle} \times 100\%$ Mean and standard deviations were calculated using Excel, and Student's t test was used for statistical calculations.

Statistical Analysis

For each group (SCV-07 at each dose, vehicle control and DTIC control), inter-group comparison was performed on the tumor volume, tumor weight and body weight, using a student's t test. P values of less than 0.05 were considered to be statistically significant.

Record Storage and Archive

All data generated in the study were collected and recorded.

Storage area: Institute of Basic Medical Sciences, PUMC & CAMS

Results and Discussion

Mortality

No deaths were found in any of the dose groups during the study.

Tumor Size

The statistical results of tumor sizes are listed in the tables. The tumor growth curves are presented in FIG. 1.

As shown in Table 2 to Table 6, on Day 3 and Day 6, tumor sizes of all groups were not measurable. The mean tumor sizes of SCV-07 treatment groups on Day 9 did not show statistical differences when compared with the vehicle control group. On Day 12, the mean tumor sizes of Group 3, Group 5 and Group 6 were significantly smaller than Group 1. Although the mean tumor size of Group 4 on Day 12 was smaller than Group 1, the results did not show statistical significance. On Day 15, the mean tumor sizes of Group 3, Group 4, Group 5 and Group 6 were smaller than Group 1, but only the results of Group 5 and Group 6 showed statistical significance. The tumor growth inhibition rate of SCV-07 of Group 6 (highest dose level) on Day 15 was 30.2%, indicating a significant (p=0.01) inhibition of tumor growth when compared to the vehicle control group. Group 5 (dose level of 1.0 mg/kg SCV-07) also showed significant tumor growth inhibition (16.5%) at the end of treatment on Day 15. The tumor growth curves also showed that the tumors grew slower in the SCV-07-treated animals when compared to the vehicle control group. Animals in positive control group have significant decrease of mean tumor sizes. Its inhibition rates of tumor growth were 96.9%, 98.8% and 95.1% on Day 9, Day 12 and Day 15, respectively. This proves that the tumor model used in this study is valid.

FIG. 1 demonstrates the decrease in growth of the tumor sizes over the time of the study in the SCV-07-treated groups when compared to the vehicle control group.

Body Weight

The statistical results of body weights are listed in the Table 8 to Table 14. As shown in the tables, there are no significant differences between SCV-07 treated groups and vehicle control group. However, the results showed a significant decrease of body weight (P<0.01) in DTIC treatment group, which is probably the result of DTIC's toxicity.

Tumor Weight

As shown in Table 7, on Day 17, the mean tumor weights of all SCV-07 treatment groups were lower than the vehicle control group. However, only the results of Group 3, Group 5 and Group 6 showed statistical significance. The tumor growth inhibition rate of Group 6 was 30.8% (p=0.015) when compared to Group 1. Group 3 and Group 5 also showed significant tumor growth inhibition of 27.5% and 23.5%, respectively. Animals in the positive control group had a significant decrease of mean tumor weights, of 85.0%.

FIG. 2 demonstrates the decrease in tumor weight at the end of the study (Day 17).

Conclusion

In conclusion, the tumor model used in this study is valid. Administration of SCV-07 once daily for 14 consecutive days via the subcutaneous route is effective against murine B16 melanoma tumor growth. Tumor weights in three test-article treated groups were significantly reduced in comparison with those of the vehicle control group. The mean animal body weights of all SCV-07 treatment groups were not significantly different from those of vehicle control group after treatment with SCV-07, supporting the lack of toxicity of the test article. However, although treatment with the positive chemotherapy control, DTIC, decreased the tumor sizes and tumor weights significantly when compared with vehicle control group, it did lead to a significant inhibition of body weight gain. The data of this study indicate that SCV-07 at dose levels of 0.01, 1.0 and 5.0 mg/kg/day for 14 days significantly reduced the B16 melanoma tumor growth without toxic effect on body weight gain.

TABLE 2

Statistical results of tumor sizes on Day 3

| Group Number | Treatment | Number of Animals | Tumor Volume (cm$^3$) (Mean ± SD) | IR (%) | p value |
|---|---|---|---|---|---|
| 1 | Vehicle Control | 10 | 0[a] | — | — |
| 2 | DTIC 50 mg/kg | 10 | 0 | — | — |
| 3 | SCV-07 0.01 mg/kg | 10 | 0 | — | — |
| 4 | SCV-07 0.1 mg/kg | 10 | 0 | — | — |
| 5 | SCV-07 1.0 mg/kg | 10 | 0 | — | — |
| 6 | SCV-07 5.0 mg/kg | 10 | 0 | — | — |

[a]tumor size was not measurable and was defined as 0.

TABLE 3

Statistical results of tumor sizes on Day 6

| Group Number | Treatment | Number of Animals | Tumor Volume (cm$^3$) (Mean ± SD) | IR (%) | p value |
|---|---|---|---|---|---|
| 1 | Vehicle Control | 10 | 0[a] | — | — |
| 2 | DTIC 50 mg/kg | 10 | 0 | — | — |
| 3 | SCV-07 0.01 mg/kg | 10 | 0 | — | — |
| 4 | SCV-07 0.1 mg/kg | 10 | 0 | — | — |
| 5 | SCV-07 1.0 mg/kg | 10 | 0 | — | — |
| 6 | SCV-07 5.0 mg/kg | 10 | 0 | — | — |

[a]tumor size was not measurable and was defined as 0.

TABLE 4

Statistical results of tumor sizes on Day 9

| Group Number | Treatment | Number of Animals | Tumor Volume (cm$^3$) (Mean ± SD) | IR (%) | p value |
|---|---|---|---|---|---|
| 1 | Vehicle Control | 10 | 0.044 ± 0.039 | — | — |
| 2 | DTIC 50 mg/kg | 10 | 0.001 ± 0.004 | 96.9 | 0.003 |
| 3 | SCV-07 0.01 mg/kg | 10 | 0.045 ± 0.042 | −4.3 | 0.920 |
| 4 | SCV-07 0.1 mg/kg | 10 | 0.039 ± 0.038 | 11.5 | 0.775 |
| 5 | SCV-07 1.0 mg/kg | 10 | 0.035 ± 0.036 | 19.7 | 0.620 |
| 6 | SCV-07 5.0 mg/kg | 10 | 0.048 ± 0.036 | −11.0 | 0.780 |

TABLE 5

Statistical results of tumor sizes on Day 12

| Group Number | Treatment | Number of Animals | Tumor Volume (cm$^3$) (Mean ± SD) | IR (%) | p value |
|---|---|---|---|---|---|
| 1 | Vehicle Control | 10 | 0.754 ± 0.503 | — | — |
| 2 | DTIC 50 mg/kg | 10 | 0.009 ± 0.020 | 98.8 | 1.9E−4 |
| 3 | SCV-07 0.01 mg/kg | 10 | 0.368 ± 0.223 | 51.2 | 0.040 |
| 4 | SCV-07 0.1 mg/kg | 10 | 0.469 ± 0.199 | 37.7 | 0.114 |
| 5 | SCV-07 1.0 mg/kg | 10 | 0.292 ± 0.169 | 61.3 | 0.013 |
| 6 | SCV-07 5.0 mg/kg | 10 | 0.340 ± 0.195 | 54.9 | 0.026 |

TABLE 6

Statistical results of tumor sizes on Day 15

| Group Number | Treatment | Number of Animals | Tumor Volume (cm$^3$) (Mean ± SD) | IR (%) | p value |
|---|---|---|---|---|---|
| 1 | Vehicle Control | 10 | 1.938 ± 0.331 | — | — |
| 2 | DTIC 50 mg/kg | 10 | 0.095 ± 0.112 | 95.1 | 2.2E−12 |
| 3 | SCV-07 0.01 mg/kg | 10 | 1.642 ± 0.549 | 15.3 | 0.162 |
| 4 | SCV-07 0.1 mg/kg | 10 | 1.786 ± 0.524 | 7.9 | 0.446 |
| 5 | SCV-07 1.0 mg/kg | 10 | 1.617 ± 0.274 | 16.5 | 0.030 |
| 6 | SCV-07 5.0 mg/kg | 10 | 1.353 ± 0.591 | 30.2 | 0.014 |

TABLE 7

Statistical results of tumor weights on Day 17

| Group Number | Treatment | Number of Animals | Tumor Weight (g) (Mean ± SD) | IR (%) | p value |
|---|---|---|---|---|---|
| 1 | Vehicle Control | 10 | 3.82 ± 0.78 | — | — |
| 2 | DTIC 50 mg/kg | 10 | 0.57 ± 0.27 | 85.0 | 2.6E−10 |
| 3 | SCV-07 0.01 mg/kg | 10 | 2.77 ± 0.88 | 27.5 | 0.011 |
| 4 | SCV-07 0.1 mg/kg | 10 | 3.59 ± 0.62 | 5.8 | 0.486 |
| 5 | SCV-07 1.0 mg/kg | 10 | 2.92 ± 0.55 | 23.5 | 0.008 |
| 6 | SCV-07 5.0 mg/kg | 10 | 2.64 ± 1.14 | 30.8 | 0.015 |

TABLE 8

Statistical results of body weights on Day 0

| Group Number | Treatment | Number of Animals | Body weight (g) (Mean ± SD) | p value |
|---|---|---|---|---|
| 1 | Vehicle Control | 10 | 21.2 ± 2.3 | — |
| 2 | DTIC 50 mg/kg | 10 | 21.5 ± 2.3 | 0.735 |
| 3 | SCV-07 0.01 mg/kg | 10 | 21.8 ± 2.2 | 0.577 |
| 4 | SCV-07 0.1 mg/kg | 10 | 21.4 ± 2.0 | 0.807 |

TABLE 8-continued

Statistical results of body weights on Day 0

| Group Number | Treatment | Number of Animals | Body weight (g) (Mean ± SD) | p value |
|---|---|---|---|---|
| 5 | SCV-07 1.0 mg/kg | 10 | 21.4 ± 2.4 | 0.857 |
| 6 | SCV-07 5.0 mg/kg | 10 | 21.9 ± 2.0 | 0.474 |

TABLE 9

Statistical results of body weights on Day 3

| Group Number | Treatment | Number of Animals | Body weight (g) (Mean ± SD) | p value |
|---|---|---|---|---|
| 1 | Vehicle Control | 10 | 21.4 ± 2.0 | — |
| 2 | DTIC 50 mg/kg | 10 | 20.9 ± 2.2 | 0.548 |
| 3 | SCV-07 0.01 mg/kg | 10 | 21.8 ± 2.2 | 0.673 |
| 4 | SCV-07 0.1 mg/kg | 10 | 21.5 ± 1.5 | 0.909 |
| 5 | SCV-07 1.0 mg/kg | 10 | 21.4 ± 2.1 | 1.000 |
| 6 | SCV-07 5.0 mg/kg | 10 | 22.0 ± 2.1 | 0.572 |

TABLE 10

Statistical results of body weights on Day 6

| Group Number | Treatment | Number of Animals | Body weight (g) (Mean ± SD) | p value |
|---|---|---|---|---|
| 1 | Vehicle Control | 10 | 22.0 ± 2.3 | — |
| 2 | DTIC 50 mg/kg | 10 | 21.4 ± 2.1 | 0.528 |
| 3 | SCV-07 0.01 mg/kg | 10 | 22.5 ± 2.1 | 0.611 |
| 4 | SCV-07 0.1 mg/kg | 10 | 22.3 ± 2.1 | 0.794 |
| 5 | SCV-07 1.0 mg/kg | 10 | 22.1 ± 2.4 | 0.926 |
| 6 | SCV-07 5.0 mg/kg | 10 | 22.7 ± 2.3 | 0.498 |

TABLE 11

Statistical results of body weights on Day 9

| Group Number | Treatment | Number of Animals | Body weight (g) (Mean ± SD) | p value |
|---|---|---|---|---|
| 1 | Vehicle Control | 10 | 21.9 ± 2.3 | — |
| 2 | DTIC 50 mg/kg | 10 | 21.5 ± 2.2 | 0.706 |
| 3 | SCV-07 0.01 mg/kg | 10 | 22.4 ± 2.4 | 0.637 |
| 4 | SCV-07 0.1 mg/kg | 10 | 22.1 ± 2.0 | 0.878 |
| 5 | SCV-07 1.0 mg/kg | 10 | 22.1 ± 2.4 | 0.852 |
| 6 | SCV-07 5.0 mg/kg | 10 | 22.4 ± 2.3 | 0.653 |

TABLE 12

Statistical results of body weights on Day 12

| Group Number | Treatment | Number of Animals | Body weight (g) (Mean ± SD) | p value |
|---|---|---|---|---|
| 1 | Vehicle Control | 10 | 23.4 ± 2.3 | — |
| 2 | DTIC 50 mg/kg | 10 | 22.1 ± 2.4 | 0.226 |
| 3 | SCV-07 0.01 mg/kg | 10 | 23.7 ± 2.8 | 0.803 |
| 4 | SCV-07 0.1 mg/kg | 10 | 23.6 ± 2.4 | 0.880 |
| 5 | SCV-07 1.0 mg/kg | 10 | 23.6 ± 2.6 | 0.865 |
| 6 | SCV-07 5.0 mg/kg | 10 | 23.4 ± 2.2 | 0.992 |

TABLE 13

Statistical results of body weights on Day 15

| Group Number | Treatment | Number of Animals | Body weight (g) (Mean ± SD) | p value |
|---|---|---|---|---|
| 1 | Vehicle Control | 10 | 24.7 ± 2.7 | — |
| 2 | DTIC 50 mg/kg | 10 | 22.2 ± 2.3 | 0.042 |
| 3 | SCV-07 0.01 mg/kg | 10 | 24.4 ± 3.2 | 0.847 |
| 4 | SCV-07 0.1 mg/kg | 10 | 24.9 ± 2.6 | 0.869 |
| 5 | SCV-07 1.0 mg/kg | 10 | 24.8 ± 2.8 | 0.905 |
| 6 | SCV-07 5.0 mg/kg | 10 | 24.3 ± 2.6 | 0.779 |

TABLE 14

Statistical results of body weights on Day 17

| Group Number | Treatment | Number of Animals | Body weight (g) (Mean ± SD) | p value |
|---|---|---|---|---|
| 1 | Vehicle Control | 10 | 26.1 ± 3.0 | — |
| 2 | DTIC 50 mg/kg | 10 | 22.9 ± 2.7 | 0.021 |
| 3 | SCV-07 0.01 mg/kg | 10 | 25.8 ± 3.5 | 0.822 |
| 4 | SCV-07 0.1 mg/kg | 10 | 26.0 ± 2.7 | 0.931 |
| 5 | SCV-07 1.0 mg/kg | 10 | 26.1 ± 3.0 | 0.988 |
| 6 | SCV-07 5.0 mg/kg | 10 | 25.7 ± 2.9 | 0.748 |

APPENDIXES

APPENDIX 1

Tumor measurements (cm) on Day 3

| | | F1 | | F2 | | F3 | | F4 | | F5 | | M1 | | M2 | | M3 | | M4 | | M5 | |
|---|---|---|---|---|---|---|---|---|---|---|---|---|---|---|---|---|---|---|---|---|---|
| Group | Treatment | L | W | L | W | L | W | L | W | L | W | L | W | L | W | L | W | L | W | L | W |
| 1 | Vehicle Control | — | — | — | — | — | — | — | — | — | — | — | — | — | — | — | — | — | — | — | — |
| 2 | DTIC 50 mg/kg | — | — | — | — | — | — | — | — | — | — | — | — | — | — | — | — | — | — | — | — |
| 3 | SCV-07 0.01 mg/kg | — | — | — | — | — | — | — | — | — | — | — | — | — | — | — | — | — | — | — | — |
| 4 | SCV-07 0.1 mg/kg | — | — | — | — | — | — | — | — | — | — | — | — | — | — | — | — | — | — | — | — |
| 5 | SCV-07 1.0 mg/kg | — | — | — | — | — | — | — | — | — | — | — | — | — | — | — | — | — | — | — | — |
| 6 | SCV-07 5.0 mg/kg | — | — | — | — | — | — | — | — | — | — | — | — | — | — | — | — | — | — | — | — |

— Not measurable

APPENDIX 2

| Group | Treatment | \multicolumn{10}{c}{Tumor volumes* (cm³) on Day 3} |
|---|---|---|---|---|---|---|---|---|---|---|---|
| | | F1 | F2 | F3 | F4 | F5 | M1 | M2 | M3 | M4 | M5 |
| 1 | Vehicle Control | — | — | — | — | — | — | — | — | — | — |
| 2 | DTIC 50 mg/kg | — | — | — | — | — | — | — | — | — | — |
| 3 | SCV-07 0.01 mg/kg | — | — | — | — | — | — | — | — | — | — |
| 4 | SCV-07 0.1 mg/kg | — | — | — | — | — | — | — | — | — | — |
| 5 | SCV-07 1.0 mg/kg | — | — | — | — | — | — | — | — | — | — |
| 6 | SCV-07 5.0 mg/kg | — | — | — | — | — | — | — | — | — | — |

*Tumor volumes were calculated using the formula "Tumor Volume = Length × Width × Width/2" based on the data listed in Appendix 1.
— Not applicable

APPENDIX 3

Tumor measurements (cm) on Day 6

| | | F1 | | F2 | | F3 | | F4 | | F5 | | M1 | | M2 | | M3 | | M4 | | M5 | |
|---|---|---|---|---|---|---|---|---|---|---|---|---|---|---|---|---|---|---|---|---|---|
| Group | Treatment | L | W | L | W | L | W | L | W | L | W | L | W | L | W | L | W | L | W | L | W |
| 1 | Vehicle Control | — | — | — | — | — | — | — | — | — | — | — | — | — | — | — | — | — | — | — | — |
| 2 | DTIC 50 mg/kg | — | — | — | — | — | — | — | — | — | — | — | — | — | — | — | — | — | — | — | — |
| 3 | SCV-07 0.01 mg/kg | — | — | — | — | — | — | — | — | — | — | — | — | — | — | — | — | — | — | — | — |
| 4 | SCV-07 0.1 mg/kg | — | — | — | — | — | — | — | — | — | — | — | — | — | — | — | — | — | — | — | — |
| 5 | SCV-07 1.0 mg/kg | — | — | — | — | — | — | — | — | — | — | — | — | — | — | — | — | — | — | — | — |
| 6 | SCV-07 5.0 mg/kg | — | — | — | — | — | — | — | — | — | — | — | — | — | — | — | — | — | — | — | — |

— Not measurable

APPENDIX 4

Tumor volumes* (cm³) on Day 6

| Group | Treatment | F1 | F2 | F3 | F4 | F5 | M1 | M2 | M3 | M4 | M5 |
|---|---|---|---|---|---|---|---|---|---|---|---|
| 1 | Vehicle Control | — | — | — | — | — | — | — | — | — | — |
| 2 | DTIC 50 mg/kg | — | — | — | — | — | — | — | — | — | — |
| 3 | SCV-07 0.01 mg/kg | — | — | — | — | — | — | — | — | — | — |
| 4 | SCV-07 0.1 mg/kg | — | — | — | — | — | — | — | — | — | — |
| 5 | SCV-07 1.0 mg/kg | — | — | — | — | — | — | — | — | — | — |
| 6 | SCV-07 5.0 mg/kg | — | — | — | — | — | — | — | — | — | — |

*Tumor volumes were calculated using the formula "Tumor Volume = Length × Width × Width/2" based on the data listed in Appendix 3.
— Not applicable

APPENDIX 5

Tumor measurements (cm) on Day 9

| | | F1 | | F2 | | F3 | | F4 | | F5 | | M1 | | M2 | | M3 | | M4 | | M5 | |
|---|---|---|---|---|---|---|---|---|---|---|---|---|---|---|---|---|---|---|---|---|---|
| Group | Treatment | L | W | L | W | L | W | L | W | L | W | L | W | L | W | L | W | L | W | L | W |
| 1 | Vehicle Control | 0.7 | 0.6 | 0.5 | 0.5 | 0.5 | 0.5 | 0.3 | 0.3 | 0.5 | 0.5 | 0.5 | 0.5 | 0.4 | 0.4 | 0.3 | 0.3 | — | — | — | — |
| 2 | DTIC 50 mg/kg | — | — | 0.3 | 0.3 | — | — | — | — | — | — | — | — | — | — | — | — | — | — | — | — |
| 3 | SCV-07 0.01 mg/kg | — | — | 0.5 | 0.5 | — | — | 0.5 | 0.5 | 0.6 | 0.6 | 0.6 | 0.6 | 0.4 | 0.4 | 0.4 | 0.3 | — | — | 0.5 | 0.5 |
| 4 | SCV-07 0.1 mg/kg | 0.5 | 0.5 | 0.5 | 0.5 | 0.5 | 0.5 | 0.6 | 0.6 | 0 | 0 | 0.3 | 0.3 | — | — | — | — | 0.3 | 0.3 | 0.5 | 0.5 |
| 5 | SCV-07 1.0 mg/kg | — | — | 0.5 | 0.5 | 0.6 | 0.6 | 0.3 | 0.3 | 0.5 | 0.5 | 0.3 | 0.3 | 0.5 | 0.5 | 0.3 | 0.3 | 0.3 | 0.3 | — | — |
| 6 | SCV-07 5.0 mg/kg | 0.5 | 0.5 | 0.5 | 0.5 | — | — | 0.6 | 0.6 | 0.5 | 0.5 | 0.5 | 0.5 | — | — | 0.5 | 0.5 | 0.5 | 0.5 | — | — |

— Not measurable

APPENDIX 6

| | | Tumor volumes* (cm³) on Day 9 | | | | | | | | | |
|---|---|---|---|---|---|---|---|---|---|---|---|
| Group | Treatment | F1 | F2 | F3 | F4 | F5 | M1 | M2 | M3 | M4 | M5 |
| 1 | Vehicle Control | 0.13 | 0.06 | 0.06 | 0.01 | 0.06 | 0.06 | 0.03 | 0.01 | — | — |
| 2 | DTIC 50 mg/kg | — | 0.01 | — | — | — | — | — | — | — | — |
| 3 | SCV-07 0.01 mg/kg | — | 0.06 | — | 0.06 | 0.11 | 0.11 | 0.03 | 0.02 | — | 0.06 |
| 4 | SCV-07 0.1 mg/kg | 0.06 | 0.06 | 0.06 | 0.11 | 0.00 | 0.01 | 0.00 | 0.00 | 0.01 | 0.06 |
| 5 | SCV-07 1.0 mg/kg | — | 0.06 | 0.11 | 0.01 | 0.06 | 0.01 | 0.06 | 0.01 | 0.01 | — |
| 6 | SCV-07 5.0 mg/kg | 0.06 | 0.06 | — | 0.11 | 0.06 | 0.06 | — | 0.06 | 0.06 | — |

*Tumor volumes were calculated using the formula "Tumor Volume = Length × Width × Width/2" based on the data listed in Appendix 5.
— Not applicable

APPENDIX 7

| | | Tumor measurements (cm) on Day 12 | | | | | | | | | | | | | | | | | | |
|---|---|---|---|---|---|---|---|---|---|---|---|---|---|---|---|---|---|---|---|---|
| | | F1 | | F2 | | F3 | | F4 | | F5 | | M1 | | M2 | | M3 | | M4 | | M5 | |
| Group | Treatment | L | W | L | W | L | W | L | W | L | W | L | W | L | W | L | W | L | W | L | W |
| 1 | Vehicle Control | 1.5 | 1.5 | 1.5 | 1.5 | 1.1 | 1.1 | 1.1 | 1.1 | 1.2 | 1.0 | 1.0 | 1.0 | 1.0 | 1.0 | 0.9 | 0.9 | 0.9 | 0.9 | 1.0 | 1.0 |
| 2 | DTIC 50 mg/kg | 0.3 | 0.3 | — | — | 0.1 | 0.1 | 0.3 | 0.3 | 0.1 | 0.1 | — | — | 0.5 | 0.5 | — | — | — | — | — | — |
| 3 | SCV-07 0.01 mg/kg | 0.1 | 0.1 | 1.0 | 0.7 | 0.1 | 0.1 | 1.0 | 1.0 | 1.0 | 0.9 | 1.1 | 1.1 | 0.9 | 0.9 | 1.1 | 0.9 | 1.0 | 1.0 | 1.1 | 1.0 |
| 4 | SCV-07 0.1 mg/kg | 1.0 | 1.0 | 1.0 | 1.0 | 1.1 | 1.0 | 1.1 | 1.1 | 0.3 | 0.3 | 1.1 | 1.1 | 0.9 | 0.9 | 1.1 | 1.1 | 1.0 | 0.9 | 0.9 | 0.9 |
| 5 | SCV-07 1.0 mg/kg | 1.0 | 0.7 | 0.9 | 0.9 | 1.0 | 1.0 | 0.1 | 0.1 | 1.0 | 1.0 | 0.8 | 0.7 | 1.0 | 1.0 | 0.7 | 0.7 | 1.0 | 0.7 | 0.8 | 0.7 |
| 6 | SCV-07 5.0 mg/kg | 1.0 | 0.9 | 1.0 | 1.0 | 0.7 | 0.7 | 0.8 | 0.8 | 1.0 | 1.0 | 0.7 | 0.7 | 0.9 | 0.9 | 0.9 | 0.9 | 1.1 | 1.1 | — | — |

— Not measurable

APPENDIX 8

| | | Tumor volumes* (cm³) on Day 12 | | | | | | | | | |
|---|---|---|---|---|---|---|---|---|---|---|---|
| Group | Treatment | F1 | F2 | F3 | F4 | F5 | M1 | M2 | M3 | M4 | M5 |
| 1 | Vehicle Control | 1.69 | 1.69 | 0.67 | 0.67 | 0.60 | 0.50 | 0.50 | 0.36 | 0.36 | 0.50 |
| 2 | DTIC 50 mg/kg | 0.01 | — | 5E−04 | 0.01 | 5E−04 | — | 0.06 | — | — | — |
| 3 | SCV-07 0.01 mg/kg | 5E−04 | 0.25 | 5E−04 | 0.50 | 0.41 | 0.67 | 0.36 | 0.45 | 0.50 | 0.55 |
| 4 | SCV-07 0.1 mg/kg | 0.50 | 0.50 | 0.55 | 0.67 | 0.01 | 0.67 | 0.36 | 0.67 | 0.41 | 0.36 |
| 5 | SCV-07 1.0 mg/kg | 0.25 | 0.36 | 0.50 | 0.00 | 0.50 | 0.20 | 0.50 | 0.17 | 0.25 | 0.20 |
| 6 | SCV-07 5.0 mg/kg | 0.41 | 0.50 | 0.17 | 0.26 | 0.50 | 0.17 | 0.36 | 0.36 | 0.67 | — |

*Tumor volumes were calculated using the formula "Tumor Volume = Length × Width × Width/2" based on the data listed in Appendix 7.
— Not applicable

APPENDIX 9

| | | Tumor measurements (cm) on Day 15 | | | | | | | | | | | | | | | | | | |
|---|---|---|---|---|---|---|---|---|---|---|---|---|---|---|---|---|---|---|---|---|
| | | F1 | | F2 | | F3 | | F4 | | F5 | | M1 | | M2 | | M3 | | M4 | | M5 | |
| Group | Treatment | L | W | L | W | L | W | L | W | L | W | L | W | L | W | L | W | L | W | L | W |
| 1 | Vehicle Control | 1.7 | 1.5 | 2 | 1.6 | 1.5 | 1.5 | 1.8 | 1.5 | 1.6 | 1.4 | 1.6 | 1.6 | 1.8 | 1.5 | 1.9 | 1.5 | 1.4 | 1.4 | 1.6 | 1.6 |
| 2 | DTIC 50 mg/kg | 0.9 | 0.9 | — | — | 1.2 | 0.5 | 0.6 | 0.6 | 0.3 | 0.3 | 0.4 | 0.4 | 0.7 | 0.7 | 0.3 | 0.3 | 0.4 | 0.4 | 0.5 | 0.5 |
| 3 | SCV-07 0.01 mg/kg | 1.3 | 1.3 | 1.4 | 1.3 | 1.4 | 1.4 | 1.8 | 1.8 | 1.5 | 1.5 | 1.8 | 1.5 | 1.4 | 1.4 | 1.4 | 1.4 | 1.4 | 1.4 | 1.8 | 1.5 |
| 4 | SCV-07 0.1 mg/kg | 1.4 | 1.4 | 1.5 | 1.5 | 1.5 | 1.5 | 1.5 | 1.5 | 1.5 | 1.4 | 2.2 | 1.7 | 1.5 | 1.4 | 1.6 | 1.6 | 1.6 | 1.4 | 1.5 | 1.5 |
| 5 | SCV-07 1.0 mg/kg | 1.4 | 1.3 | 1.5 | 1.5 | 1.6 | 1.5 | 1.4 | 1.3 | 1.5 | 1.5 | 1.7 | 1.3 | 1.6 | 1.6 | 1.5 | 1.5 | 2 | 1.3 | 2.1 | 1.3 |
| 6 | SCV-07 5.0 mg/kg | 1.3 | 1.3 | 1.4 | 1.4 | 1.6 | 1.5 | 1.6 | 1.3 | 1.6 | 1.4 | 1.5 | 1.4 | 1.8 | 1.6 | 1.3 | 1.3 | 1.5 | 1.4 | — | — |

— Not measurable

APPENDIX 10

| | | Tumor volumes* (cm³) on Day 15 | | | | | | | | | |
|---|---|---|---|---|---|---|---|---|---|---|---|
| Group | Treatment | F1 | F2 | F3 | F4 | F5 | M1 | M2 | M3 | M4 | M5 |
| 1 | Vehicle Control | 1.91 | 2.56 | 1.69 | 2.03 | 1.57 | 2.05 | 2.03 | 2.14 | 1.37 | 2.05 |
| 2 | DTIC 50 mg/kg | 0.36 | — | 0.15 | 0.11 | 0.01 | 0.03 | 0.17 | 0.01 | 0.03 | 0.06 |
| 3 | SCV-07 0.01 mg/kg | 1.37 | 1.69 | 1.69 | 1.69 | 1.47 | 3.18 | 1.47 | 2.05 | 1.57 | 1.69 |
| 4 | SCV-07 0.1 mg/kg | 1.18 | 1.69 | 1.80 | 1.18 | 1.69 | 1.44 | 2.05 | 1.69 | 1.69 | 1.77 |

APPENDIX 10-continued

Tumor volumes* (cm³) on Day 15

| Group | Treatment | F1 | F2 | F3 | F4 | F5 | M1 | M2 | M3 | M4 | M5 |
|---|---|---|---|---|---|---|---|---|---|---|---|
| 5 | SCV-07 1.0 mg/kg | 1.10 | 1.37 | 1.80 | 1.35 | 1.57 | 1.47 | 2.30 | 1.10 | 1.47 | — |
| 6 | SCV-07 5.0 mg/kg | 1.91 | 2.56 | 1.69 | 2.03 | 1.57 | 2.05 | 2.03 | 2.14 | 1.37 | 2.05 |

*Tumor volumes were calculated using the formula "Tumor Volume = Length × Width × Width/2" based on the data listed in Appendix 9.
— Not applicable

APPENDIX 11

Tumor weights (g) on Day 17

| Group | Treatment | F1 | F2 | F3 | F4 | F5 | M1 | M2 | M3 | M4 | M5 |
|---|---|---|---|---|---|---|---|---|---|---|---|
| 1 | Vehicle Control | 4.15 | 3.66 | 2.6 | 4.75 | 3.47 | 4.6 | 3.27 | 4.85 | 2.90 | 3.90 |
| 2 | DTIC 50 mg/kg | 0.70 | 0.29 | 0.98 | 0.78 | 0.5 | 0.37 | 0.915 | 0.18 | 0.46 | 0.54 |
| 3 | SCV-07 0.01 mg/kg | 1.55 | 2.04 | 2.24 | 3.71 | 3.21 | 4.57 | 2.29 | 2.50 | 2.77 | 2.80 |
| 4 | SCV-07 0.1 mg/kg | 2.46 | 4.08 | 4.03 | 3.93 | 3.52 | 4.47 | 2.86 | 3.74 | 3.10 | 3.73 |
| 5 | SCV-07 1.0 mg/kg | 2.69 | 2.67 | 4.06 | 2.66 | 3.25 | 2.25 | 2.55 | 2.58 | 3.58 | 2.89 |
| 6 | SCV-07 5.0 mg/kg | 1.94 | 3.15 | 2.97 | 2.80 | 2.85 | 2.45 | 3.78 | 2.02 | 4.30 | 0.15 |

APPENDIX 12

Body weights (g) on Day 0

| Group | Treatment | F1 | F2 | F3 | F4 | F5 | M1 | M2 | M3 | M4 | M5 |
|---|---|---|---|---|---|---|---|---|---|---|---|
| 1 | Vehicle Control | 18.7 | 19.3 | 18.5 | 20.5 | 19 | 23.1 | 21.7 | 23.5 | 24.8 | 22.8 |
| 2 | DTIC 50 mg/kg | 18.5 | 21.6 | 19.8 | 19.3 | 20 | 24.9 | 24.1 | 23.6 | 20.4 | 23.2 |
| 3 | SCV-07 0.01 mg/kg | 19.7 | 20.2 | 19.3 | 21.3 | 19.5 | 21.2 | 23.9 | 22.7 | 24.7 | 25.1 |
| 4 | SCV-07 0.1 mg/kg | 20.8 | 19.3 | 18.8 | 20.2 | 19 | 23.1 | 22.1 | 23.7 | 23.5 | 23.8 |
| 5 | SCV-07 1.0 mg/kg | 20.6 | 20.3 | 20 | 17.8 | 18.5 | 23.1 | 22.3 | 23.6 | 25.4 | 22.2 |
| 6 | SCV-07 5.0 mg/kg | 19.3 | 20.6 | 20.4 | 20.4 | 20.6 | 22.4 | 24.8 | 21.4 | 24.5 | 24.6 |

APPENDIX 13

Body weights (g) on day 3

| Group | Treatment | F1 | F2 | F3 | F4 | F5 | M1 | M2 | M3 | M4 | M5 |
|---|---|---|---|---|---|---|---|---|---|---|---|
| 1 | Vehicle Control | 20.1 | 20.1 | 18.8 | 20.5 | 19.5 | 23.2 | 21 | 23.5 | 24.8 | 22.7 |
| 2 | DTIC 50 mg/kg | 17.8 | 20.5 | 19.2 | 18.6 | 19.9 | 24.6 | 23.2 | 22.4 | 20.1 | 22.2 |
| 3 | SCV-07 0.01 mg/kg | 19.9 | 20.6 | 20 | 20.6 | 19.1 | 21.8 | 23.3 | 22.6 | 25.3 | 25 |
| 4 | SCV-07 0.1 mg/kg | 20.6 | 20.4 | 20 | 20.3 | 19.8 | 22 | 22.1 | 23.4 | 23.4 | 23.1 |
| 5 | SCV-07 1.0 mg/kg | 20.4 | 20 | 19.7 | 19.4 | 18.5 | 23.4 | 22.7 | 22.7 | 25 | 22.4 |
| 6 | SCV-07 5.0 mg/kg | 19.1 | 21 | 20.5 | 20.7 | 20.5 | 22.2 | 24.8 | 21 | 24.8 | 24.9 |

APPENDIX 14

Body weights (g) on Day 6

| Group | Treatment | F1 | F2 | F3 | F4 | F5 | M1 | M2 | M3 | M4 | M5 |
|---|---|---|---|---|---|---|---|---|---|---|---|
| 1 | Vehicle Control | 19.8 | 19.8 | 19.3 | 21.4 | 19.7 | 23.7 | 22.2 | 24.8 | 25.6 | 23.6 |
| 2 | DTIC 50 mg/kg | 18.3 | 20.3 | 20.7 | 19 | 20.5 | 24.8 | 23.9 | 22.8 | 20.5 | 22.7 |
| 3 | SC-07 0.01 mg/kg | 21.1 | 21.2 | 20.3 | 21.6 | 20.1 | 22 | 24.2 | 23 | 25.8 | 25.6 |
| 4 | SCV-07 0.1 mg/kg | 20.8 | 20.6 | 19.9 | 20.8 | 19.8 | 23.3 | 23.4 | 24.4 | 24.5 | 25 |
| 5 | SCV-07 1.0 mg/kg | 20.8 | 20.4 | 20.1 | 19.7 | 19.2 | 24.8 | 23 | 23.9 | 26.2 | 22.8 |
| 6 | SCV-07 5.0 mg/kg | 20.3 | 21.5 | 21.3 | 21.4 | 21.2 | 22.6 | 26.1 | 21.1 | 25.6 | 25.9 |

APPENDIX 15

Body weights (g) on Day 9

| Group | Treatment | F1 | F2 | F3 | F4 | F5 | M1 | M2 | M3 | M4 | M5 |
|---|---|---|---|---|---|---|---|---|---|---|---|
| 1 | Vehicle Control | 19.8 | 20.2 | 19.3 | 21.2 | 19.5 | 23.9 | 21.7 | 24.8 | 25.3 | 23.5 |
| 2 | DTIC 50 mg/kg | 19 | 20.3 | 20.3 | 19 | 21.3 | 24.8 | 24.2 | 23.6 | 20.1 | 22.8 |

APPENDIX 15-continued

Body weights (g) on Day 9

| Group | Treatment | F1 | F2 | F3 | F4 | F5 | M1 | M2 | M3 | M4 | M5 |
|---|---|---|---|---|---|---|---|---|---|---|---|
| 3 | SCV-07 0.01 mg/kg | 20.1 | 21 | 20 | 21.8 | 19.5 | 22.5 | 24.5 | 23.1 | 25.7 | 26 |
| 4 | SCV-07 0.1 mg/kg | 20.5 | 21.2 | 19.4 | 20.9 | 19.6 | 22.6 | 23.5 | 24 | 24 | 25 |
| 5 | SCV-07 1.0 mg/kg | 20.4 | 20.4 | 19.4 | 19.7 | 19.9 | 24.3 | 23 | 24.6 | 26.2 | 23.3 |
| 6 | SCV-07 5.0 mg/kg | 19.7 | 21.4 | 20.9 | 20.9 | 20.4 | 22.9 | 25.6 | 21.1 | 25.3 | 25.7 |

APPENDIX 16

Body weights (g) on Day 12

| Group | Treatment | F1 | F2 | F3 | F4 | F5 | M1 | M2 | M3 | M4 | M5 |
|---|---|---|---|---|---|---|---|---|---|---|---|
| 1 | Vehicle Control | 21.3 | 21.9 | 20.7 | 21.9 | 21.3 | 25.7 | 23.5 | 26.6 | 26 | 25.4 |
| 2 | DTIC 50 mg/kg | 19.4 | 20.7 | 20.4 | 19.4 | 21.3 | 26.1 | 25 | 24 | 21.2 | 23.7 |
| 3 | SCV-07 0.01 mg/kg | 21.1 | 21.3 | 20.9 | 23.1 | 20.4 | 24.6 | 25.9 | 24.3 | 27.6 | 28 |
| 4 | SCV-07 0.1 mg/kg | 21.5 | 21.7 | 21.6 | 21.7 | 20.5 | 24.9 | 25.3 | 26 | 25.8 | 26.9 |
| 5 | SCV-07 1.0 mg/kg | 22.4 | 21.5 | 21.1 | 20.8 | 20.8 | 26.3 | 24.7 | 26.4 | 27.9 | 24.3 |
| 6 | SCV-07 5.0 mg/kg | 21.4 | 22.1 | 22.1 | 22.2 | 21.5 | 23.6 | 26.8 | 21.9 | 26.5 | 26.3 |

APPENDIX 17

Body weights (g) on Day 15

| Group | Treatment | F1 | F2 | F3 | F4 | F5 | M1 | M2 | M3 | M4 | M5 |
|---|---|---|---|---|---|---|---|---|---|---|---|
| 1 | Vehicle Control | 22.2 | 24.1 | 21.5 | 22.5 | 21.6 | 27.4 | 24.2 | 28.5 | 27.6 | 26.9 |
| 2 | DTIC 50 mg/kg | 19.6 | 20.3 | 20.9 | 19.7 | 21.6 | 25.6 | 24.7 | 24.3 | 21.2 | 24.2 |
| 3 | SCV-07 0.01 mg/kg | 21 | 20.9 | 21.2 | 24.5 | 21.1 | 25.2 | 26.2 | 26.1 | 28.5 | 29.2 |
| 4 | SCV-07 0.1 mg/kg | 22.2 | 23.4 | 22.3 | 23.1 | 21.3 | 27.7 | 26.7 | 26.4 | 26.8 | 28.6 |
| 5 | SCV-07 1.0 mg/kg | 22.2 | 23 | 22.2 | 22.3 | 21.9 | 27.2 | 26.5 | 27.6 | 29.6 | 25.5 |
| 6 | SCV-07 5.0 mg/kg | 21.5 | 23.2 | 23.1 | 22.9 | 21.5 | 24.5 | 29 | 23 | 27.8 | 26.6 |

APPENDIX 18

Body weights (g) on Day 17

| Group | Treatment | F1 | F2 | F3 | F4 | F5 | M1 | M2 | M3 | M4 | M5 |
|---|---|---|---|---|---|---|---|---|---|---|---|
| 1 | Vehicle Control | 23.2 | 26.6 | 23 | 23.7 | 22.8 | 29.1 | 25.3 | 31.2 | 28.2 | 28.1 |
| 2 | DTIC 50 mg/kg | 19.8 | 20.8 | 21.6 | 19.8 | 22.2 | 27 | 25.8 | 25.2 | 21.5 | 25.5 |
| 3 | SCV-07 0.01 mg/kg | 22.7 | 21.4 | 22.4 | 25.2 | 22.4 | 27.3 | 28 | 27.3 | 30.2 | 31 |
| 4 | SCV-07 0.1 mg/kg | 22.8 | 24.4 | 23.1 | 24.1 | 23.8 | 28 | 27.9 | 27.3 | 28.3 | 30.4 |
| 5 | SCV-07 1.0 mg/kg | 23.9 | 23.4 | 24 | 23.2 | 23.1 | 27.2 | 28.2 | 29.6 | 31.6 | 27.2 |
| 6 | SCV-07 5.0 mg/kg | 22.5 | 24.9 | 23.8 | 23.4 | 22.8 | 26.2 | 31.5 | 25.2 | 29.3 | 27.3 |

The invention claimed is:

1. A method of treating or reducing melanoma or a metastasis thereof, or growth of melanoma cells or metastases thereof, in a subject in need thereof, comprising administering to the subject an effective amount of an immunomodulator compound of formula A

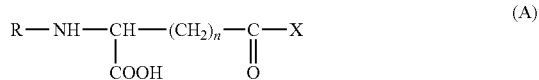

(A)

wherein, n is 1 or 2; R is hydrogen, C2-10 acyl, or C1-6 alkyl; and X is L-tryptophan or D-tryptophan, so as to treat or reduce said melanoma or metastasis thereof in the subject, or treat or reduce growth of said melanoma cells or metastases thereof in the subject.

2. The method of claim 1 wherein said compound is γ-D-glutamyl-L-tryptophan.

3. The method of claim 1 wherein said compound is administered at a dosage within a range of about 0.001-1000 mg.

4. The method of claim 1 wherein said compound is administered at a dosage within a range of about 0.01-100 mg.

5. The method of claim 1 wherein said compound is administered at a dosage within a range of about 0.00001-100 mg/kg subject body weight.

6. The method of claim 1 wherein said compound is administered at a dosage within a range of about 0.01-10 mg/kg subject body weight.

7. The method of claim 1 wherein said compound is γ-D-glutamyl-L-tryptophan, and is administered at a dosage within a range of about 0.001-1000 mg.

8. The method of claim 1 wherein said compound is γ-D-glutamyl-L-tryptophan and is administered at a dosage within a range of about 0.00001-100 mg/kg subject body weight.

9. The method of claim 2 wherein said treatment is for primary melanoma.

10. The method of claim 9 wherein said compound is administered at a dosage within a range of about 0.001-1000 mg.

11. The method of claim 9 wherein said compound is administered at a dosage within a range of about 0.1-100 mg.

12. The method of claim 9 wherein said compound is administered at a dosage within a range of about 0.00001-100 mg/kg subject body weight.

13. The method of claim 9 wherein said compound is administered at a dosage within a range of about 0.01-10 mg/kg subject body weight.

14. The method of claim 2 wherein said treatment is for a melanoma metastasis.

15. The method of claim 14 wherein said compound is administered at a dosage within a range of about 0.001-1000 mg.

16. The method of claim 14 wherein said compound is administered at a dosage within a range of about 0.1-100 mg.

17. The method of claim 14 wherein said compound is administered at a dosage within a range of about 0.00001-100 mg/kg subject body weight.

18. The method of claim 14 wherein said compound is administered at a dosage within a range of about 0.01-10 mg/kg subject body weight.

19. The method of claim 11 wherein said dosage is about 10 mg.

20. The method of claim 16 wherein said dosage is about 10 mg.

21. The method of claim 1 wherein said subject is a human patient.

\* \* \* \* \*